(12) United States Patent
Shambaugh et al.

(10) Patent No.: US 10,780,206 B2
(45) Date of Patent: Sep. 22, 2020

(54) PUMP TO MOTOR CONNECTION SYSTEM

(71) Applicant: HeartWare, Inc., Miami Lakes, FL (US)

(72) Inventors: Charles R. Shambaugh, Coral Gables, FL (US); Jeffrey A. Larose, Sunrise, FL (US); Mustafa E. Taskin, Cooper City, FL (US)

(73) Assignee: HeartWare, Inc., Miami Lakes, FL (US)

( * ) Notice: Subject to any disclaimer, the term of this patent is extended or adjusted under 35 U.S.C. 154(b) by 241 days.

(21) Appl. No.: 15/676,281

(22) Filed: Aug. 14, 2017

(65) Prior Publication Data
US 2019/0046703 A1 Feb. 14, 2019

(51) Int. Cl.
*A61M 1/10* (2006.01)
*A61M 1/12* (2006.01)
*F04D 13/02* (2006.01)
*F04D 29/06* (2006.01)

(52) U.S. Cl.
CPC ........ *A61M 1/1012* (2014.02); *A61M 1/1029* (2014.02); *A61M 1/125* (2014.02); *F04D 13/021* (2013.01); *F04D 29/061* (2013.01)

(58) Field of Classification Search
CPC .............. A61M 1/1012; A61M 1/1029; A61M 1/12–125
See application file for complete search history.

(56) References Cited

U.S. PATENT DOCUMENTS

| | | | | |
|---|---|---|---|---|
| 5,376,114 | A | * | 12/1994 | Jarvik ................ A61M 1/102 128/898 |
| 2012/0178986 | A1 | * | 7/2012 | Campbell ............. A61M 1/101 600/16 |

FOREIGN PATENT DOCUMENTS

| | | |
|---|---|---|
| EP | 0764448 A3 | 5/1997 |
| GB | 2239675 A | 7/1991 |
| WO | 94/09835 A1 | 5/1994 |

OTHER PUBLICATIONS

International Search Report and Written Opinion dated Apr. 18, 2018, for corresponding International Application No. PCT/US2017/046743; International Filing Date: Aug. 14, 2017 consisting of 11-pages.

* cited by examiner

*Primary Examiner* — Eric D. Bertram
(74) *Attorney, Agent, or Firm* — Christopher & Weisberg, P.A.

(57) ABSTRACT

A connection system for an implantable blood pump including a pump housing having an impeller disposed therein and a motor housing including a motor disposed therein, the motor housing spaced a distance from the pump housing. A flexible outer sheath couples the pump housing to the motor housing, the outer sheath defining a maximum total length between 7 and 10 centimeters. An inner shaft is coaxial with the outer sheath and couples the motor to the impeller.

10 Claims, 6 Drawing Sheets

PUMP TO MOTOR CONNECTION SYSTEM

TECHNICAL FIELD

The present invention relates to a connection system for an implantable blood pump.

BACKGROUND

Implantable blood pumps, such as intravascular and intraventricular blood pumps, may be miniaturized blood pumps used as mechanical circulatory support devices to move blood from the heart to the rest of the body. Intravascular blood pumps may be percutaneously or surgically implanted into a patient's vascular system to provide left heart support or right heart support. In the alternative, intraventricular blood pumps may be implanted into a ventricle of the patient to provide left heart support or right heart support. In operation, the blood pump includes an inflow portion that draws blood from a source, such as the right ventricle, left ventricle, right atrium, or left atrium of a patient's heart and impels the blood through an outflow portion into an artery, such as the patient's ascending aorta or peripheral artery. Known blood pumps may be limited to providing either left-side support or right-side support.

In addition to the inflow portion, and the outflow portion, blood pumps typically include a blood pump connected to a motor. In particular, the blood pump is disposed in a housing which also includes a rotating impeller to impel the blood. The impeller may include one or more vanes or flow channels to impel blood from the inflow portion to the outflow portion of the blood pump. The motor spins the impeller, thus providing the pumping action. Many known blood pumps connect the motor to the impeller using a connection system having a long and semi-rigid shaft that is difficult to align during implantation and through the vascular exit site. For example, in order to couple the blood pump to an exterior motor, known shafts may include a length that exceeds 12 centimeters, the average length of an ascending aorta in a human body. Such long and semi-rigid shafts do not sufficiently flex to allow the motor to move relative to the blood pump housing to selectively align the blood pump within a specified location of the heart. In addition, relatively long shafts pose a higher risk of infection and require frequent maintenance, such as added lubrication, to safeguard the integrity of shaft.

SUMMARY

A pump to motor connection system for an implantable blood pump including a pump housing having an impeller disposed therein and a motor housing having a motor disposed therein, the motor housing being spaced a distance from the pump housing. A flexible outer sheath couples the pump housing to the motor housing, the outer sheath defining a maximum total length between 7 and 10 centimeters. An inner shaft is coaxial with the outer sheath, the inner shaft coupling the motor to the impeller.

In another aspect of this embodiment, the system includes a motor shaft extending at least partially within the outer sheath.

In another aspect of this embodiment, the pump housing defines a total length between 2 and 4 centimeters.

In an additional aspect of this embodiment, the motor housing defines a total length between 2 and 4 centimeters.

In yet another aspect of this embodiment, the outer sheath includes a pliable member and a cover member surrounding the pliable member.

In another aspect of this embodiment, the inner shaft is flexible and includes a plurality of steel members defining a coil.

In an additional aspect of this embodiment, the outer sheath includes a proximal portion and a distal portion, the proximal portion being rigidly coupled to the pump housing and the distal portion being rigidly coupled to the motor housing, the pump housing being moveable relative to the motor housing.

In another aspect of this embodiment, the implantable blood pump includes a bearing and a thrust washer each coupled to the inner shaft.

In another aspect of this embodiment, the thrust washer defines a lubrication channel.

In another aspect of this embodiment, the outer sheath and the inner shaft define a conduit therebetween, the conduit including a biocompatible fluid retained therein.

In another embodiment, the pump to motor connection system for an implantable blood pump includes a pump housing having an impeller disposed therein and a motor housing having a motor disposed therein, the motor housing being spaced a distance from the pump housing. The pump housing and the motor housing are sized to be received within at least one of the group consisting of a chamber of a heart and a blood vessel exterior to the heart. A sheath movably couples the pump housing relative to the motor housing, the sheath made of a malleable material. A flexible inner shaft is coaxial with and moveable relative to the sheath, the inner shaft extending through the pump housing and being connected to the impeller and the motor.

In another aspect of this embodiment, the sheath defines a maximum total length between 7 and 10 centimeters.

In another aspect of this embodiment, the sheath defines a total length of 9 centimeters.

In yet another aspect of this embodiment, the sheath defines the distance between the pump housing and the motor housing.

In an additional aspect of this embodiment, the pump housing and the motor housing each define a length between 2 and 4 centimeters.

In another aspect of this embodiment, the inner sheath is made of a plurality of steel members defining a coil.

In another aspect of this embodiment, the pump housing and the motor housing are selectively moveable relative to the at least one of the group consisting of a chamber of a heart and a blood vessel exterior to the heart.

In another aspect of this embodiment, the at least one of the group consisting of a chamber of a heart and a blood vessel exterior to the heart includes a left ventricle and an aorta.

In yet another aspect of this embodiment, the system includes a bearing and a thrust washer each coupled to the inner shaft.

In another embodiment, the pump to motor connection system for an implantable blood pump includes a pump housing having an impeller and a diffuser disposed therein, the pump housing defining a maximum total length between 2 and 4 centimeters and a motor housing having a motor disposed therein, the motor housing defining a maximum total length between 2 and 4 centimeters and being moveable relative to the pump housing. The connection system also includes a flexible outer sheath having a proximal portion and a distal portion, the proximal portion extending from the pump housing and the distal portion extending from the motor housing, the outer sheath defining a maximum total length between 7 and 10 centimeters. A flexible inner shaft is coaxial with outer sheath, the inner shaft extending at least partially through the motor housing and being connected to the impeller, the diffuser, and the motor, the outer sheath and the inner shaft defining a conduit therebetween, the conduit including a biocompatible fluid retained therein.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

Figure 1:
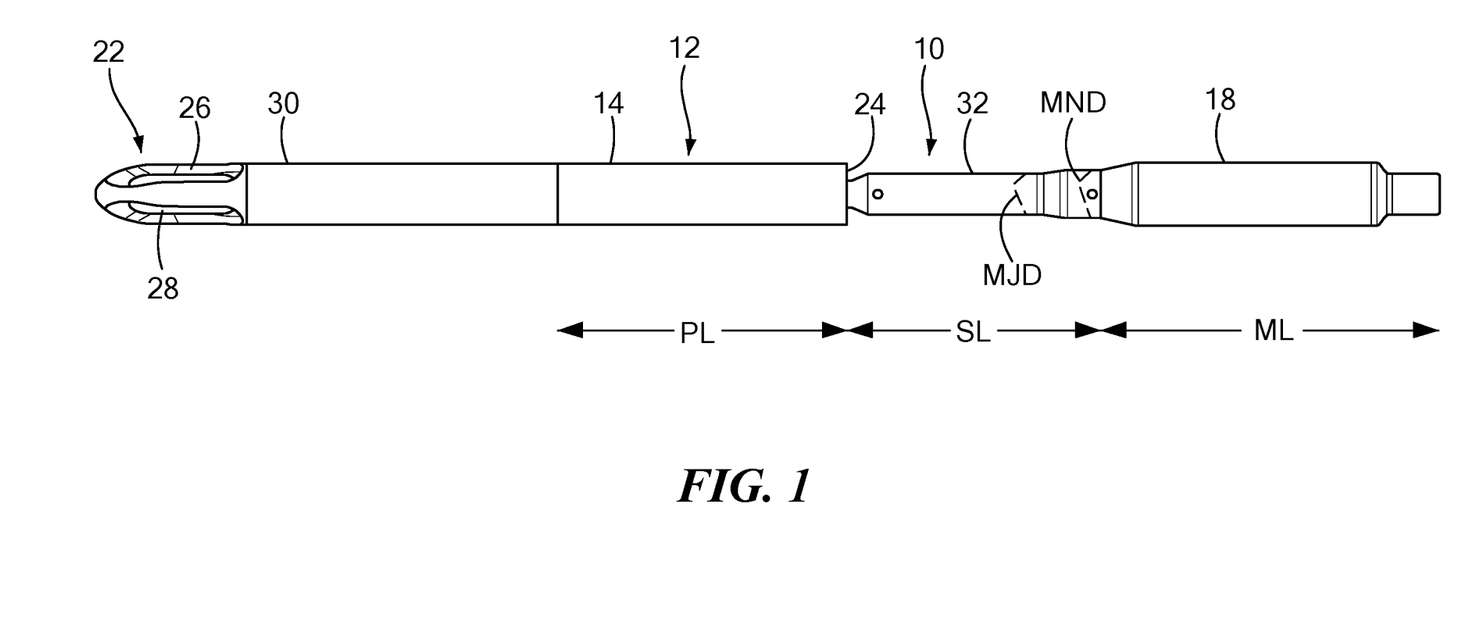
FIG. 1 is a side view of a pump to motor connection system including a pump housing and a motor housing coupled to each other by an outer sheath and an inner shaft in accordance with the principles of the present invention.

Referring now to the drawings in which like reference designators refer to like elements there is shown in FIG. 1 an exemplary pump to motor connection system for an implantable blood pump constructed in accordance with the principles of the present application and designated generally "10." The connection system 10 may include an implantable blood pump 12 that is intravascular and/or intraventricular, such as implanted within the vascular system and/or a ventricle of a mammalian heart, such as a human heart, to provide left and/or right heart support for a patient.

Figure 2:
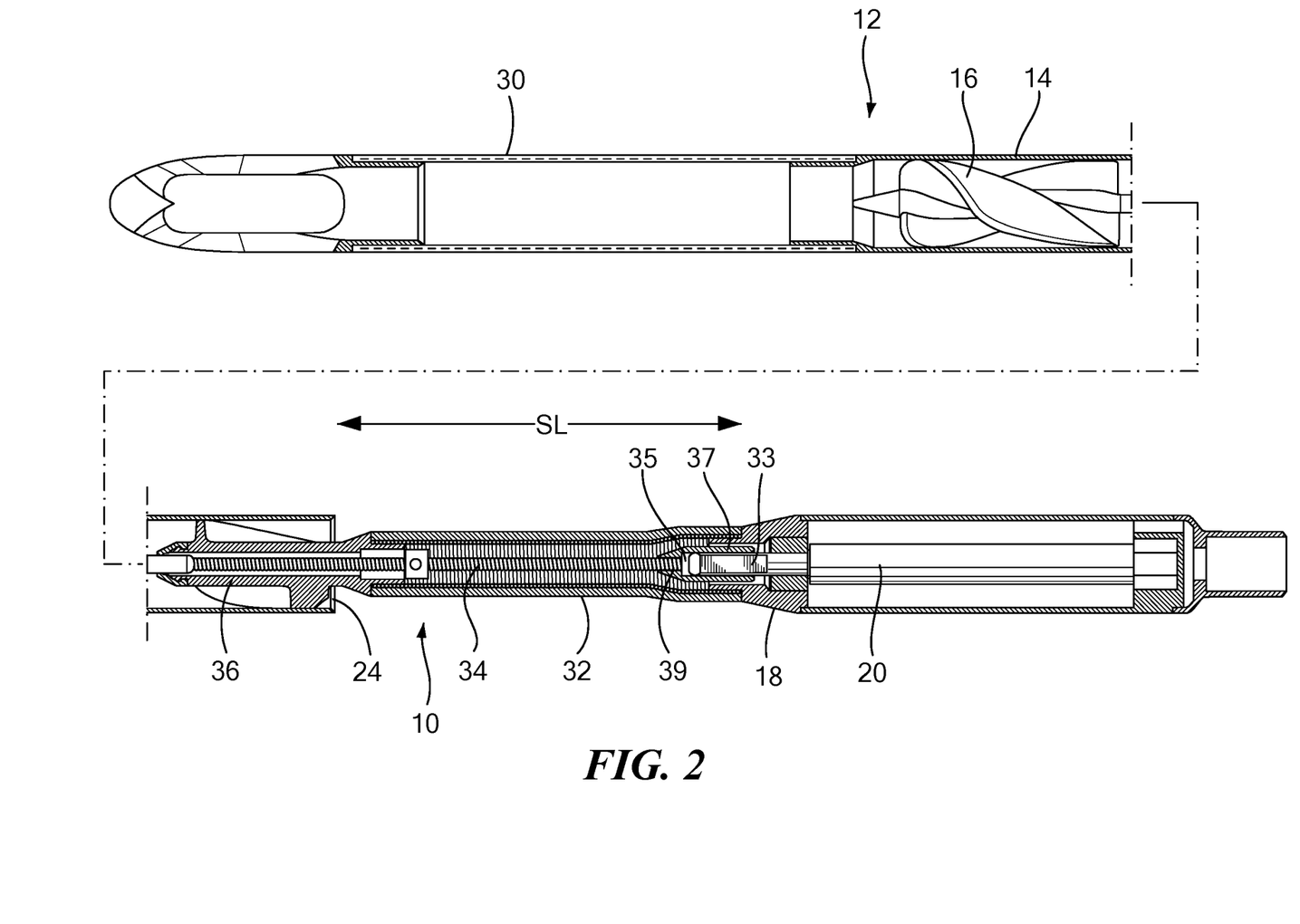
FIG. 2 is a side cross-sectional view of the pump to motor connection system shown in FIG. 1.

With reference to FIGS. 1 and 2, depicting a side view and a side cross-sectional view, respectively, the connection system 10 includes a pump housing 14 having an impeller 16 disposed therein and a motor housing 18 including a motor 20 disposed therein. The impeller 16 includes vanes and/or flow channels which rotate to impel blood from an inflow portion 22 to an outflow portion 24 of the pump housing 14. Although FIG. 1 depicts the inflow portion 22 including a cannula tip 26 defining three inlet apertures 28 and an inflow cannula 30 coupled to the cannula tip 26, other configurations of the inflow portion 22 may also be utilized with more or less inlet apertures 28. The pump housing 14 defines the outflow portion 24 with an aperture for blood to exit the blood pump 12 and circulate throughout a patient's body.

The motor housing 18 may be spaced a distance from the pump housing 14. As shown in FIG. 1, the distance may be defined by a length of a flexible outer sheath 32, generally designated as "SL", which couples the pump housing 14 to the motor housing 18. For example, the outer sheath 32 may define a maximum total length between 7 and 10 centimeters. In one configuration, the total length of the outer sheath 32 is 9 centimeters.

The outer sheath 32 may include a tapered region which tapers in a direction toward the pump housing 14 to define a minor diameter, generally designated as "MND," between 0.33-0.39 centimeters and a major diameter, generally designated as "MJD," between 0.40-0.46 centimeters. The outer sheath 32 allows the pump housing 14 to move relative to the motor housing 18 to assist with alignment during implantation of the blood pump 12. For example, the outer sheath 32 may assist with aligning the blood pump 12 within a low curvature ascending aorta for left-side heart support and within a right atrium or vena cava for right-side heart support. Alignment within the heart may occur using a guide catheter or another method of implantation.

With reference to FIG. 2, an inner shaft 34 may be disposed within the blood pump 12 that is coaxial with the outer sheath 32. The inner shaft 34 may extend through the outer sheath 32 to couple the motor 20 to the impeller 16, thus causing the motor 20 to rotate the impeller 16 to impel the blood. In one configuration, the motor 20 may include a motor shaft 33 extending from the motor housing 18 at least partially within the outer sheath 32. The motor shaft 33 may be slidably received within a first channel 35 defined by a coupling member 37, such as a support bracket, extending between the outer sheath 32 and the motor housing 18. The coupling member 37 may define a second channel 39 for receiving the inner shaft 34, such that the inner shaft 34 is in communication with the motor shaft 33 for rotation. In one configuration, an opposing end of the inner shaft 34 may be coupled to the impeller 16, such as through welding.

Other coupling arrangements between the inner shaft 34, the motor 20, and the impeller 16 may also be used, such as a slot and pin connection, bearings, and the like.

In one configuration, the motor 20 may be powered by a drive circuit (not shown) including electrical coils for applying electrical current to the motor 20. Alternative power sources may also be utilized. In one configuration, the inner shaft 34 may also extend through a diffuser 36 disposed within the pump housing 14 to improve the hydraulic efficiency of the blood pump 12. Similar to the outer sheath 32, the inner shaft 34 may be flexible to provide for improved alignment within the heart during implantation. In one configuration, the diameter of the pump housing 14 and the motor housing 18 is between 0.50-0.57 centimeters, however the diameter may vary outside of this range.

The pump housing 14 and the motor housing 18 are sized to be received within a chamber of a heart and/or a blood vessel exterior to the heart. For example, the pump housing 14 and the motor housing 18 may each define a total length, generally designated as "PL" and "ML," respectively in FIG. 1, between 2 and 4 centimeters. In one exemplary configuration, because the outer sheath 32 may define the maximum total length between 7 and 10 centimeters, the blood pump 12 may be implanted entirely within the left ventricle and an ascending aorta of an adult patient having an ascending aorta with an average length of approximately 12 centimeters. In one configuration, the pump housing 14 is sized to be received within the left ventricle and the motor housing 18 is sized to be received within the ascending aorta. In another example, the pump housing 14 is sized to be received within the right ventricle and the motor housing 18 is sized to be received downstream of a pulmonary valve. Additionally, the pump housing 14 is sized to be received within the left atrium, which may be beneficial for treating certain conditions, such as pulmonary hypertension. In another example, the pump housing 14 and the motor housing 18 are sized to be received within the heart with an outflow cannula being utilized to bridge the patient's aortic valve. Such examples are not intended to be limiting as the blood pump 12 is sized to be received in other configurations within the heart and the exterior blood vessel, depending on whether the patient would benefit from left and/or right heart support.

Figure 3:
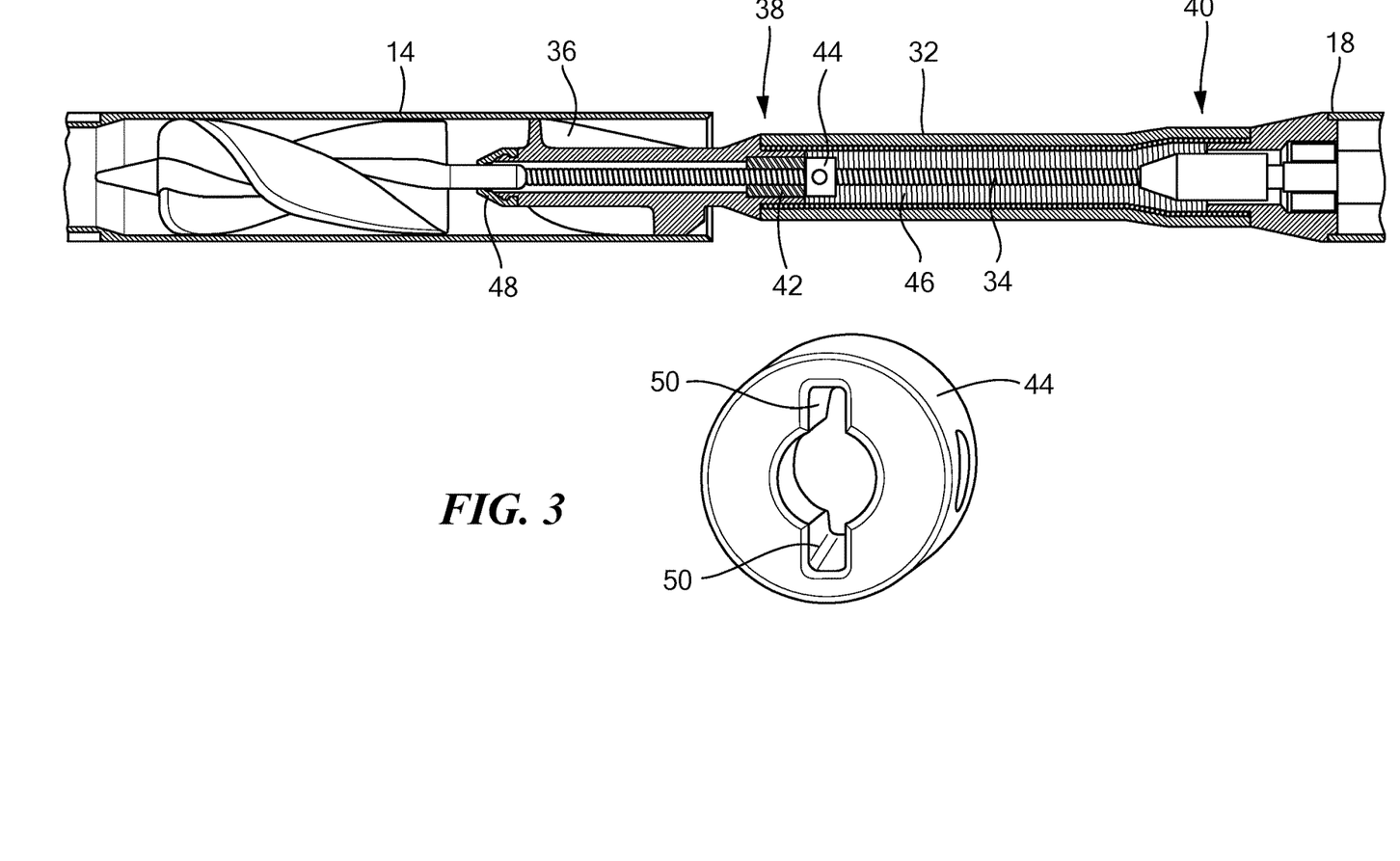
FIG. 3 is a close-up side cross-sectional view of the pump to motor connection system shown in FIG. 2.

With reference to FIG. 3, the outer sheath 32 may include a proximal portion 38 and a distal portion 40. The proximal portion 38 may be rigidly coupled to the pump housing 14 and the distal portion 40 may be rigidly coupled to the motor housing 18, such as through the use of welding, brackets, or another coupling mechanism which creates a rigid connection. In an exemplary configuration, the diffuser 36 may extend from the pump housing 14 and the proximal portion 38 of the outer sheath 32 may be coupled to the diffuser 36. A bearing 42 and a thrust washer 44 may each be coupled to the inner shaft 34 to create a thrust bearing for supporting an axial force of the inner shaft 34. The bearing 42 may bridge the connection between the diffuser 36 and the outer sheath 32.

Figure 4:
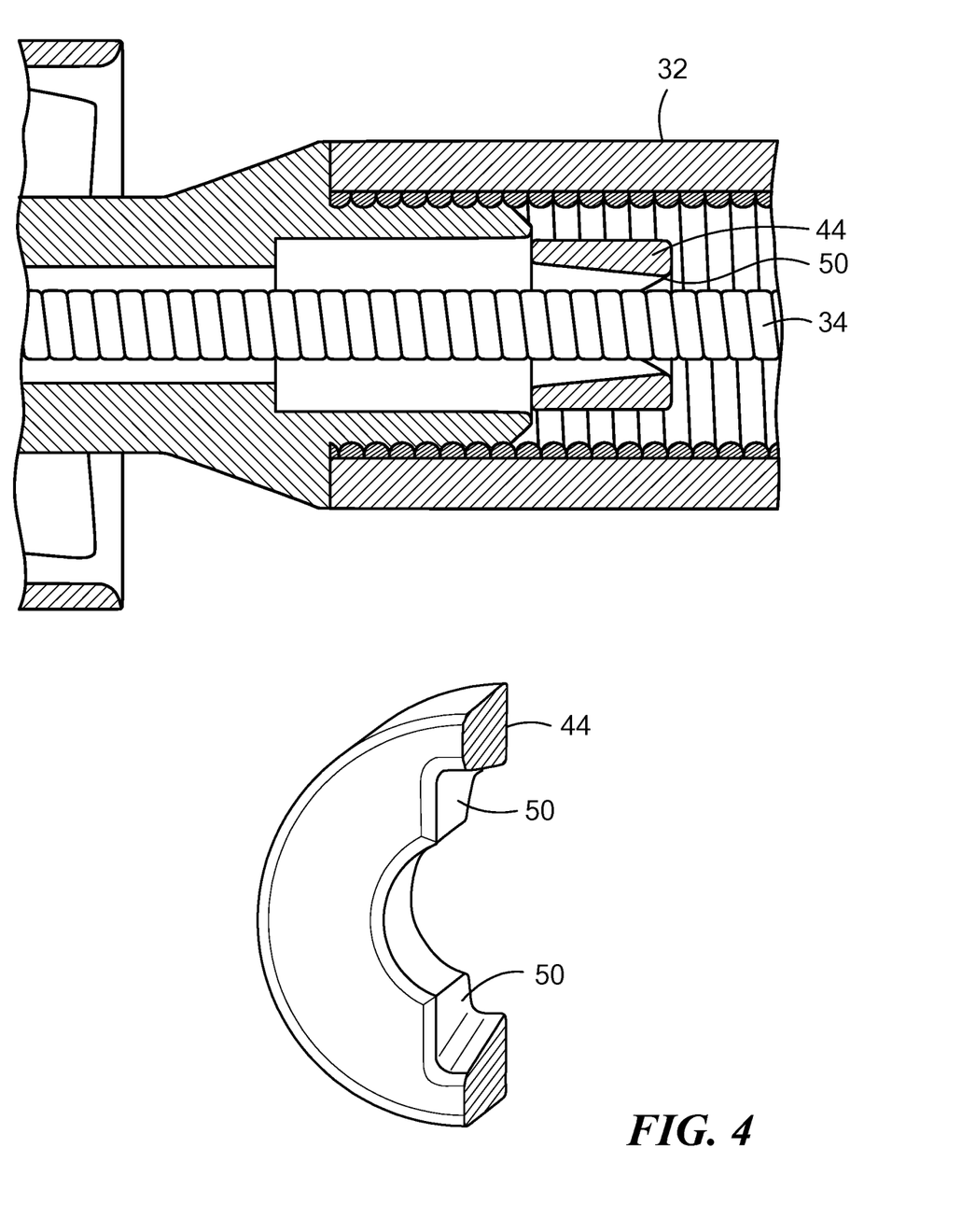
FIG. 4 is a close-up side cross-sectional view of the pump to motor connection system shown in FIG. 2.

In one configuration, the outer sheath 32 and the inner shaft 34 define a conduit 46 therebetween for retaining a biocompatible fluid, such as dextrose, to add lubrication to the inner shaft 34. A flexible seal 48 may be coupled to the diffuser 36 to contain the biocompatible fluid within the conduit 46. As a further source of lubrication, the thrust washer 44 may define a pair of lubrication grooves 50 adjacent the inner shaft 34 which allow the fluid to surround and thus lubricate the inner shaft 34. For example, as shown in the cross-sectional view of FIG. 4, the lubrication grooves 50 may extend through the thrust washer 44, thus permitting the fluid to travel along and around the inner shaft 34 for lubrication.

Figure 5:
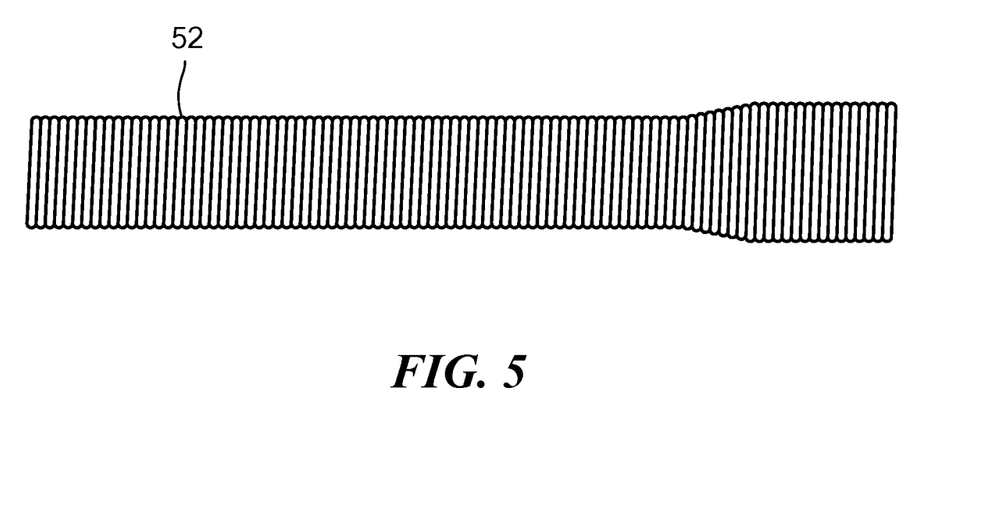
FIG. 5 is a side view of a pliable member of the outer sheath of FIG. 1.
Figure 6:
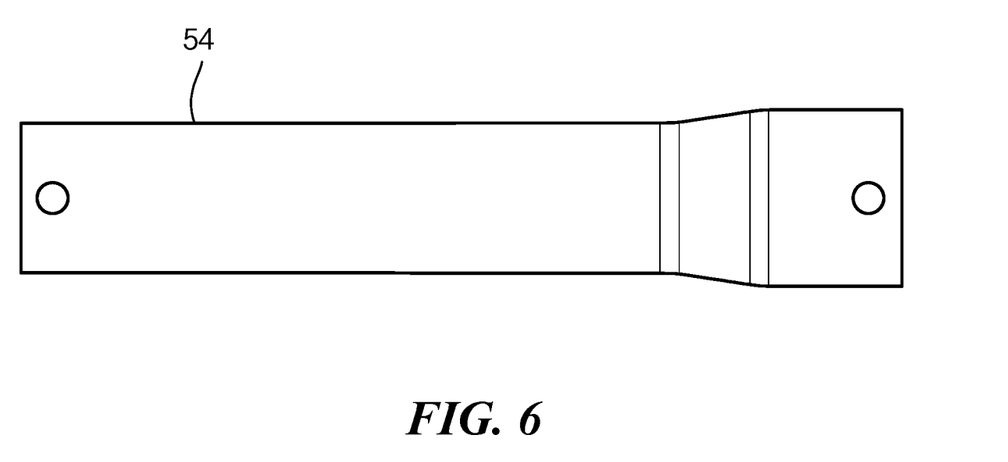
FIG. 6 is a side view of a cover member of the outer sheath of FIG. 1 for surrounding the pliable member shown in FIG. 4.

The outer sheath 32 may me made of a malleable material, such as a biocompatible polymeric material, stainless steel, or another material that flexes and bends to allow for alignment within the heart and/or the exterior blood vessel. For example, with reference to FIGS. 5 and 6, the outer sheath 32 may include a pliable member 52 (FIG. 5), such as a spring, coil, or the like configured to be disposed within a cover member 54 (FIG. 6). The cover member 54 may be a silicone mold which surrounds the pliable member 52 to preserve the integrity of the pliable member 52, while permitting the flexing and bending.

Figure 7:
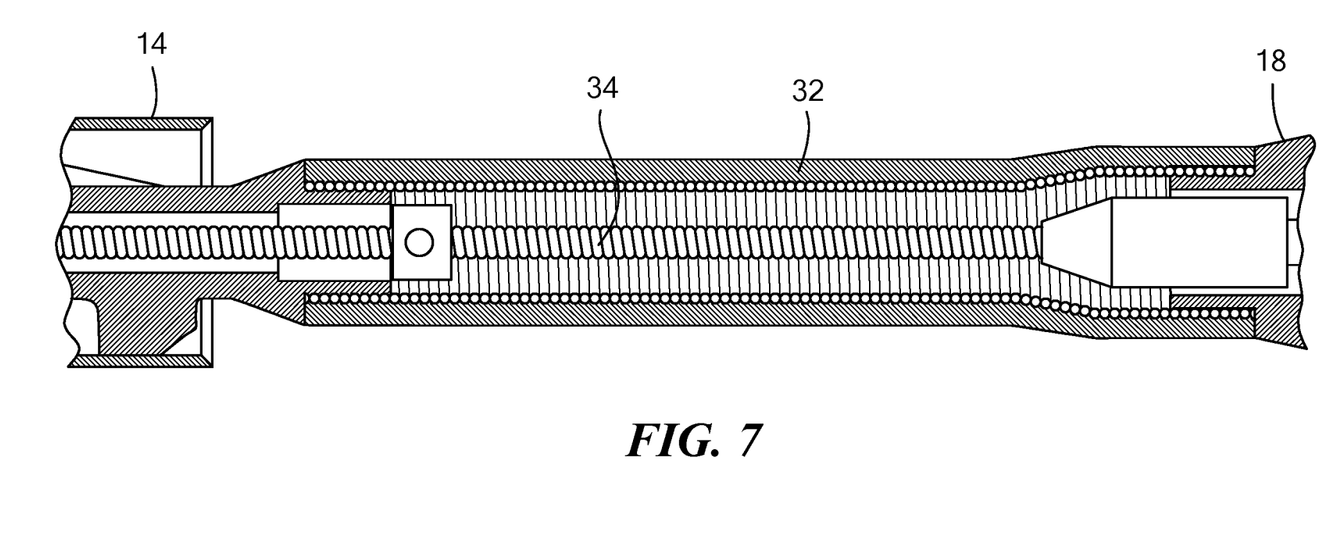
FIG. 7 is a close-up side cross-sectional view of the inner shaft of the pump to motor connection system shown in FIG. 2.

In one configuration, as shown in FIG. 7, the inner shaft 34 is coaxial with and moveable relative to the outer sheath 32 as a result of the inner shaft 34 being made of two or more steel members wound together to define a coil. In one configuration the inner shaft 34 may be made of an inner coil and an outer coil. For example, the inner coil may be made of a stainless-steel wire that is right-hand wound and the outer coil may be made of the stainless-steel wire that is left-hand wound to assist with providing appropriate torque for operation of the blood pump 12. In addition, the materials forming the outer sheath 32 and the inner shaft 34 provide a surgeon with the ability to selectively move the pump housing 14 and the motor housing 18 relative to each other during implantation of the blood pump 12.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A pump to motor connection system for an implantable blood pump, comprising:
   a pump housing including an impeller and a diffuser disposed therein;
   a motor housing including a motor disposed therein, the motor housing being spaced a distance from the pump housing;
   a flexible outer sheath coupling the pump housing to the motor housing, the outer sheath defining a maximum total length between 7 and 10 centimeters, a distal end of the flexible outer sheath being directly engaged with a proximal end of the diffuser;
   an inner shaft coaxial with the outer sheath, the inner shaft coupling the motor to the impeller;
   a distal end of the inner shaft being coupled to a proximal end of the impeller; and
   a bearing and a thrust washer each coupled to the inner shaft, the thrust washer being proximal to the diffuser, the bearing being disposed between the diffuser and the thrust washer.

2. The system of claim 1, further comprising a motor shaft extending at least partially within the outer sheath.

3. The system of claim 1, wherein the pump housing defines a total length between 2 and 4 centimeters.

4. The system of claim 3, wherein the motor housing defines a total length between 2 and 4 centimeters.

5. The system of claim 1, wherein the outer sheath includes a pliable member and a cover member surrounding the pliable member.

6. The system of claim 5, wherein the inner shaft is flexible and includes a plurality of steel members wound together in opposite directions to define a coil.

7. The system of claim 1, wherein the outer sheath includes a proximal portion and a distal portion, the proximal portion being rigidly coupled to the pump housing and the distal portion being rigidly coupled to the motor housing, the pump housing being moveable relative to the motor housing.

8. The system of claim 1, wherein the thrust washer defines a lubrication groove.

9. The system of claim 1, wherein the outer sheath and the inner shaft define a conduit therebetween, the conduit including a biocompatible fluid retained therein.

10. A pump to motor connection system for an implantable blood pump, comprising:

a pump housing including an impeller and a diffuser disposed therein;

a motor housing including a motor disposed therein, the motor housing being spaced a distance from the pump housing;

a flexible outer sheath directly engaged to the diffuser and coupling the pump housing to the motor housing, the outer sheath defining a maximum total length between 7 and 10 centimeters;

an inner shaft coaxial with the outer sheath, the inner shaft coupling the motor to the impeller;

a distal end of the inner shaft being coupled to a proximal end of the impeller; and a bearing and a thrust washer each coupled to the inner shaft, the thrust washer being proximal to the diffuser, the bearing being disposed between the diffuser and the thrust washer.

\* \* \* \* \*